United States Patent [19]

Bentley

[11] 4,196,075
[45] * Apr. 1, 1980

[54] MEMBRANE FLUID TRANSFER METHOD AND APPARATUS

[75] Inventor: Donald J. Bentley, Newport Beach, Calif.

[73] Assignee: Bentley Laboratories, Inc., Irvine, Calif.

[*] Notice: The portion of the term of this patent subsequent to Jun. 13, 1995, has been disclaimed.

[21] Appl. No.: 951,166

[22] Filed: Oct. 13, 1978

Related U.S. Application Data

[63] Continuation of Ser. No. 721,523, Sep. 8, 1976, abandoned.

[51] Int. Cl.² .................. A61M 1/03; B01D 13/00; B01D 31/00
[52] U.S. Cl. .................. 210/19; 210/23 R; 210/185; 210/349; 210/321 B; 422/48
[58] Field of Search .................. 210/19, 22, 23 R, 349, 210/185, 456, 321 B, 494 M, 497.1; 422/48, 46

[56] References Cited

U.S. PATENT DOCUMENTS

| | | | |
|---|---|---|---|
| Re. 27,510 | 10/1972 | Hoeltzenbein | 210/321 B |
| 3,332,746 | 7/1967 | Claff et al. | 422/48 |
| 3,489,647 | 1/1970 | Kolobow | 210/22 |
| 3,515,640 | 6/1970 | Rudlin | 210/321 B |
| 3,615,024 | 10/1971 | Michaels | 210/490 |
| 3,927,981 | 12/1975 | Viannay et al. | 422/48 |
| 3,934,982 | 1/1976 | Arp | 422/48 |
| 3,998,593 | 12/1976 | Yoshida et al. | 422/48 |
| 4,094,792 | 6/1978 | Bentley | 210/321 B |

OTHER PUBLICATIONS

"A New Disposable Memb. Oxygenator with Integral Heat Exchange" Bramson et al., Journ. of Thoracic and Card. Surgery, vol. 50, #3, 9/1965.

*Primary Examiner*—Charles N. Hart
*Assistant Examiner*—David Sadowski
*Attorney, Agent, or Firm*—Lyon & Lyon

[57] ABSTRACT

A method and apparatus for fluid transfer across a membrane wherein transfer fluid is passed through the interior of a wrapped, permeable, flattened, tubular membrane and fluid to be processed is passed through passageways formed between the wrappings of the tubular membrane. The exhaustion of transfer fluid begins at the completion of a process fluid pumping stroke and ends at the initiation of the pumping stroke. In a preferred embodiment the method and apparatus are utilized to oxygenate blood.

24 Claims, 6 Drawing Figures

MEMBRANE FLUID TRANSFER METHOD AND APPARATUS

This is a continuation of application Ser. No. 721,523, filed Sept. 8, 1976, now abandoned.

BACKGROUND OF THE INVENTION

1. Field of the Invention

This invention relates to a method and apparatus for fluid transfer across a membrane.

2. Description of the Prior Art

Successful extracorporeal circulation has previously been obtained by using bubble oxygenators, disc oxygenators, screen type and filming type oxygenators. All of such oxygenation devices are dependent upon a blood-gas interface in which the blood and oxygen are in intimate contact in order to achieve the necessary gas exchange whereby oxygen is transferred into the blood and carbon dioxide and other waste products are removed from the blood.

It has been hypothesized that the blood-gas interface inherent in all such designs is responsible in part for hemolysis and protein denaturization. Such systems which are dependent upon a direct blood-gas interface are limited to a relatively short term use and are rarely used beyond an eight hour period. Thus, a need arose for the gas transfer between blood and gas without direct contact.

Indirect blood-gas transfer has been attempted across a gas permeable membrane positioned between the blood and the gas in order to reduce or minimize trauma to the blood and extend the periods of use. However, such membrane oxygenator devices have an efficiency which deteriorates with time, and are much more expensive than the earlier bubble types mentioned and are thus not used in the majority of cases except when long term support is necessary. One of the chief causes for the deterioration of the efficiency of such gas transfer membrane type oxygenators is due to the varying differential pressure across the membrane which contributes to the build-up of contaminents such as water vapor along the membrane surface on the oxygen side of the membrane and the protein, platelets and other cells that build-up on the blood side of the membrane.

In addition, most of the prior art membrane oxygenators have been based on a silicon rubber membrane. Silicon rubber was chosen because of its permeability to oxygen and carbon dioxide in thin sections. However, silicon rubber is very difficult to deal with as it tends to stick to itself and thus requires special handling techniques which increase the cost of such devices and it is very difficult to manufacture in thin section with complete integrity. Moreover, in many of the present membrane oxygenator systems used, the blood-gas interface is not totally eliminated in that there are various reservoirs utilized in the systems which have a blood-gas interface at the surface.

SUMMARY OF THE INVENTION

In accordance with this invention a method and apparatus of modifying the properties of a fluid to be processed is provided wherein substances to be added or removed from said process fluid are transferred across a membrane. In an embodiment for the oxygenation of blood, oxygen is passed through the interior of a wrapped, permeable, flattened tubular membrane and blood is passed through the passageways formed between the wrappings of the tubular membrane. The exhalation of excess oxygen and carbon dioxide removed from the blood may be controlled in response to the blood pumping stroke and ends at the initiation of the pumping stroke. A build-up of the oxygen pressure within the tubular membrane thus corresponds to the blood pressure build-up on the exterior of the membrane so as to maintain a relatively constant differential pressure across the membrane's surface. The blood pressure is maintained at a level slightly higher than the oxygen pressure in order to prevent gas from directly entering the blood. Further, the rapid exhalation of oxygen and carbon dioxide removes contaminants from the membrane interior surface such as water vapor and improves gas transfer across the membrane.

The blood is pumped in a pulsatile fashion through the device and to the patient's arterial system through the passageways created between adjacent membrane envelopes. The membranes are wrapped around a suitable substrate and sealed which allows fluid flow passed the substrate on the inside of the envelope and support for the membrane so that under external pressure the external surface of the membrane assumes a gently undulating and/or pocketed surface. Pulsatile blood flow with its continuously varying velocity profile, causes gentle turbulence and mixing which improves the efficiency of transfer and scrubs the membrane surface to minimize the deposition of proteins, platelets and other cells which reduces the loss in efficiency with time due to such deposition.

DESCRIPTION OF THE PREFERRED EMBODIMENTS

Figure 1:
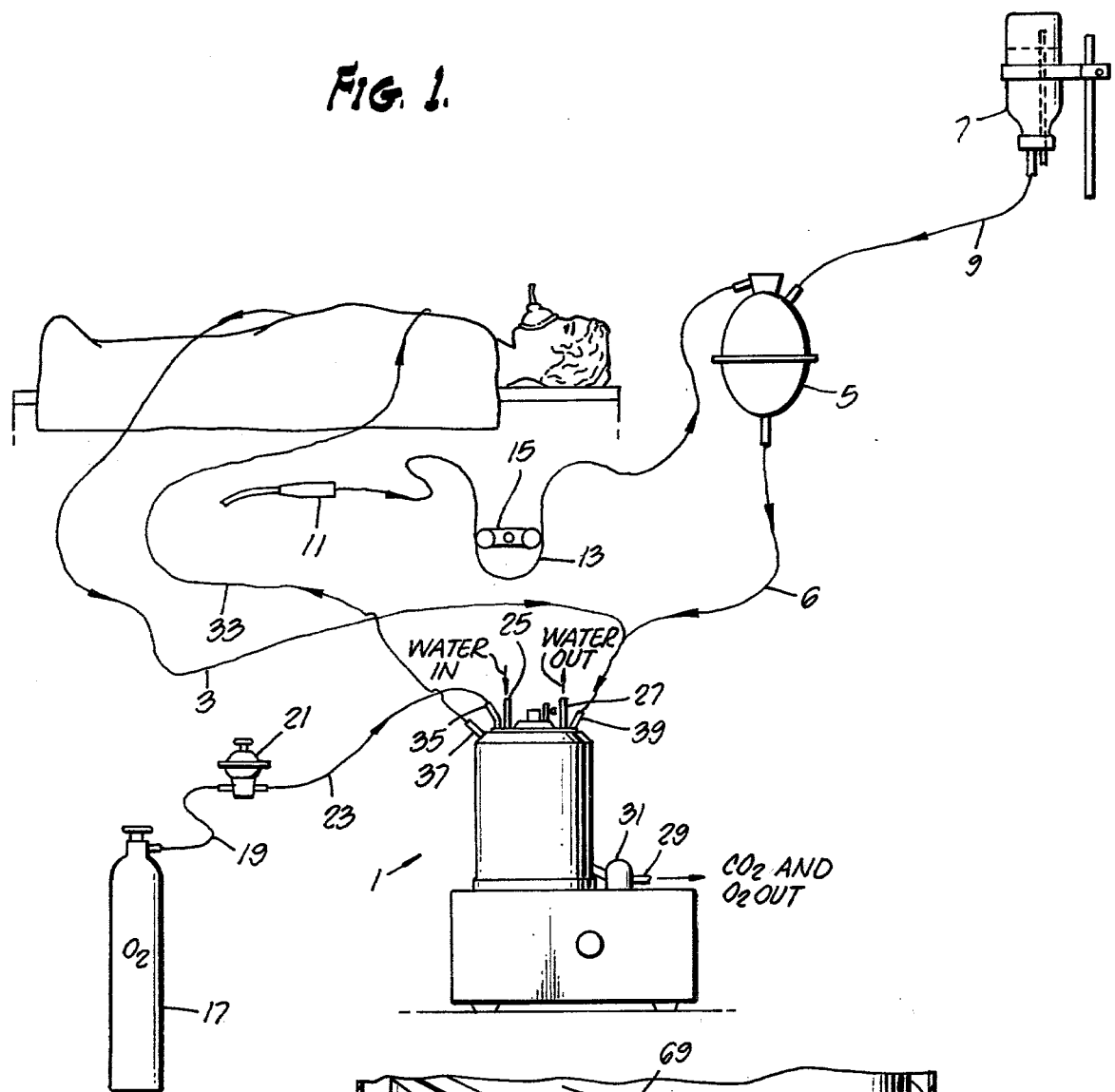
FIG. 1 is a schematic view illustrating the use of the present invention.

Referring now to FIG. 1, a device generally referred to as 1 is shown. Venous blood is shown flowing into the device 1, from the patient by means of a line 3. Additional blood flows from a cardiotomy reservoir 5 by means of line 6. For a fuller description of a cardiotomy reservoir, reference is made to my U.S. Pat. No. 3,507,395. The cardiotomy reservoir 5 may be fed from an external blood source 7 by means of a line 9 or may be extracted from a patient by means of an atraumatic fluid handling device referred to as 11 which causes blood to flow into the cardiotomy reservoir through line 13. Illustrative of a force pumping such blood through the atraumatic fluid handling device into the cardiotomy reservoir 5 is a pumping means 15.

In the embodiment wherein the device is utilized as a blood oxygenator, an oxygen source 17 passes oxygen through a line 19 into a regulator 21 from whence the regulated oxygen passes in to blood oxygenator 1 by means of a line 23. A heat transfer medium such as water passes into the blood oxygenator 1 by means of an inlet 25. The heat transfer medium exists the blood oxygenator at outlet 27. The oxygen and carbon dioxide outlet is illustrated in FIG. 1 at 29, the outlet being located downstream of a valving means 31. The oxygenated blood is returned to a patient by means of line 33 which is connected to the oxygenator by means of a venous blood outlet 37. The oxygen inlet line at 23 is connected to the oxygenator at inlet 35 and the incoming venous blood enters the oxygenator 1 by means of a venous blood line connection 39.

Figure 2:
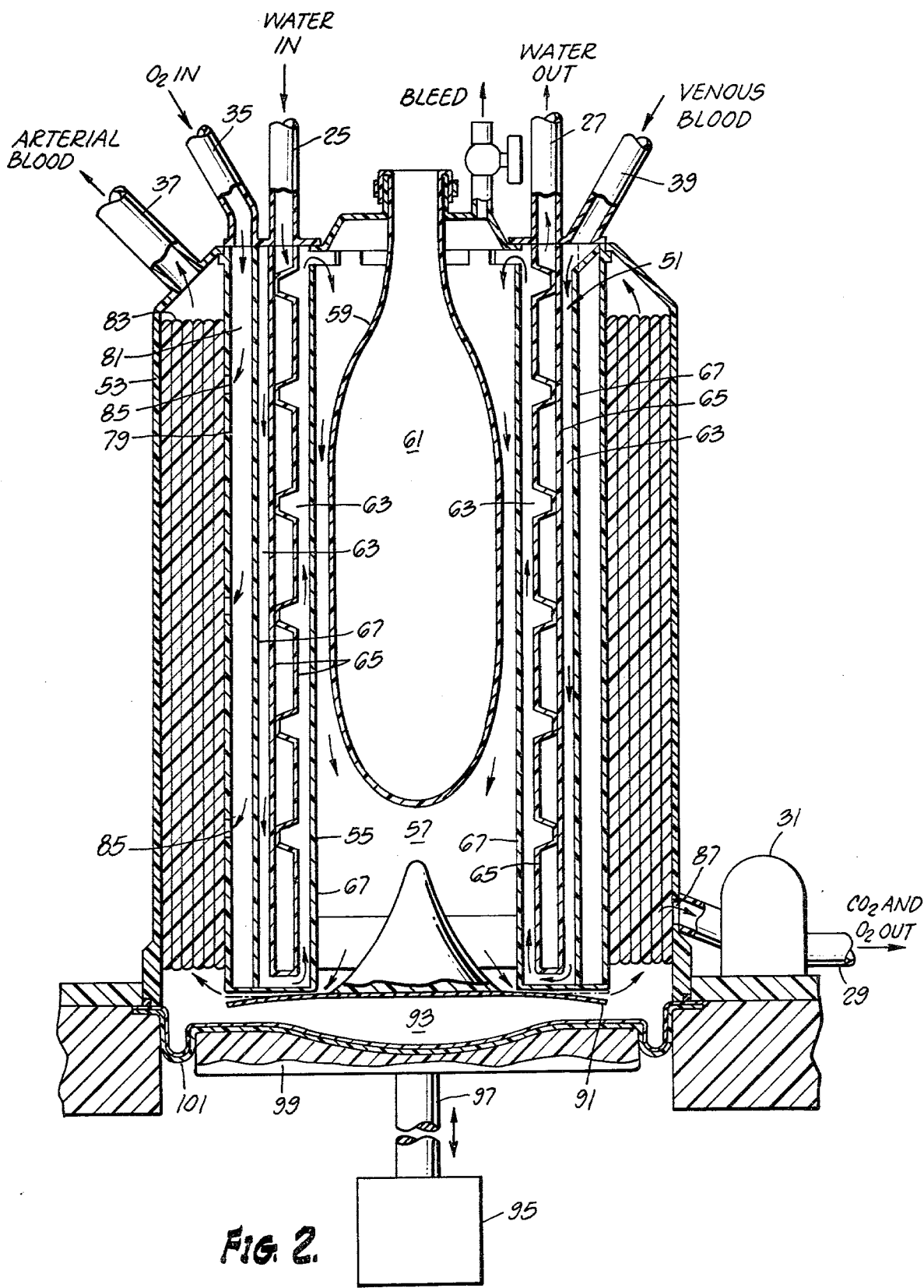
FIG. 2 is a cross-sectional view of the present invention.

Referring now to FIG. 2, a more detailed description of the blood oxygenator 1 will be given. A heat exchanger generally referred to as 51 is annularly positioned within the oxygenator housing 53 of the oxygenator 1. It is to be noted that while a heat exchanger 51 is utilized in a preferred embodiment of the method and apparatus, such a heat exchanger is not required in order to practice this invention. The inner wall 55 of the annular heat exchanger 51 forms an atrium chamber 57. In the atrium chamber 57 and occupying a portion of the chamber volume, is a flaccid, impermeable membrane enclosure 59. The interior 61 of the membrane enclosure 59 may be filled with a gaseous substance. The venous blood flows into the oxygenator 1 through venous blood inlet 39 and into a passageway to 63 formed by annular walls 65 and 67. In a preferred embodiment, the heat exchanger 51 is of a double wall construction wherein walls 67 and 65 provide for a double pass of the blood through the passage 63 in countercurrent directions. The heat transfer media, which in a preferred embodiment is water, is passed into the blood oxygenator 1 by means of inlet 25 and is removed from the oxygenator 1 by means of an outlet 37. The heat transfer media passes through the heat exchanger 51 in a double helix passage as is more clearly defined by reference to FIG. 3.

Figure 3:
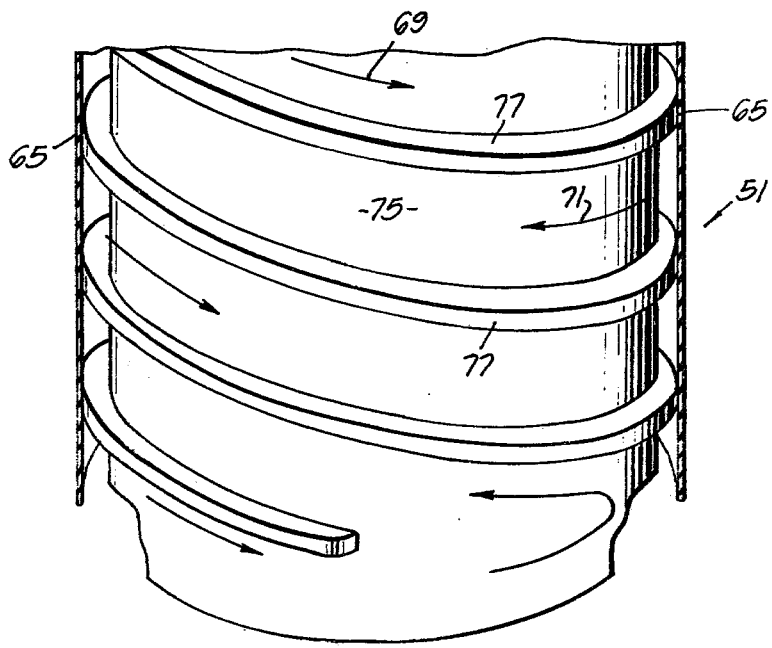
FIG. 3 is a partial cross-sectional view of the present invention.

Referring now to FIG. 3, the countercurrent heat transfer media flow produced by the double helix is illustrated by directional arrows 69 and 71 which show the heat transfer media flowing in countercurrent directions about the double helix produced by the wall member 65 and the core member 75 which has a spiral baffle 77 which separates the countercurrent heat transfer medium passages. Such a double helix design allows inlet means and outlet means at same end.

Referring again to FIG. 2, the incoming oxygen passes into the oxygenator 1 by means of oxygen inlet 35 and passes through an annular passage 81 defined by walls 79 and 67 through openings 85 into the interior of the flattened tubular membrane 83 which is spirally wrapped about wall 79 and may be enclosed at its extremity by the housing 53 of the oxygenator 1.

A leaf valve 91 may be positioned at the base of the atrium 57, the valve 91 allowing blood to flow into a ventricle 93 during the suction stroke of a reciprocating piston 97 driven by a driving means 95. The ventricle 93 is partially formed by a flaccid, impermeable membrane 101 adapted about a diaphragm 99 which may be mounted on shaft 97.

The tubular membrane 83 is preferably formed from an asymetric, thermoplastic material having permeability to oxygen and carbon dioxide. Other membranes with appropriate permeability may also be used. The wrapper tubular membrane 83 is preferably potted or otherwise adhered to the walls 53 and 79 and a plurality of holes are provided such as at 85 and 87 to allow for the entrance and exit of the gas respectively. A control level 31 regulates the exit of excess oxygen and the carbon dioxide removed from the blood.

Figure 4:
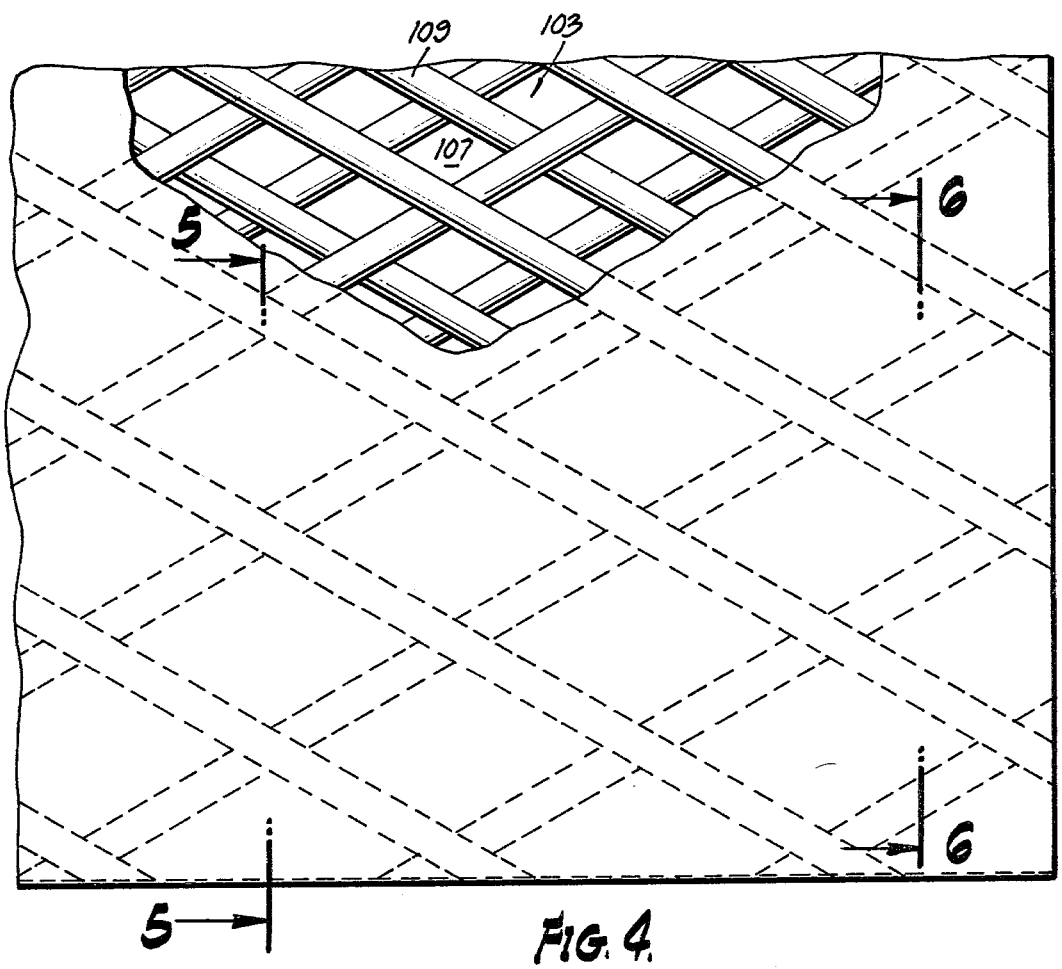
FIG. 4 is a partial cross-sectional view of the present invention.
Figure 5:
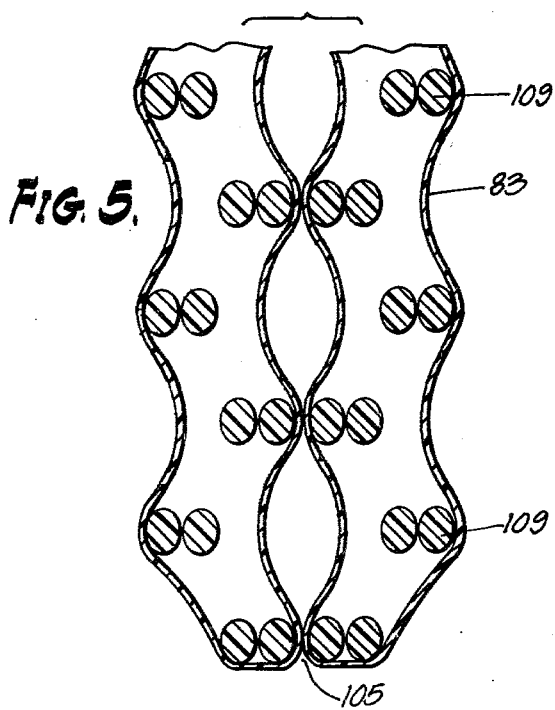
FIGS. 5 and 6 are cross-sectional views taken about 5—5 and 6—6 of FIG. 4.
Figure 6:
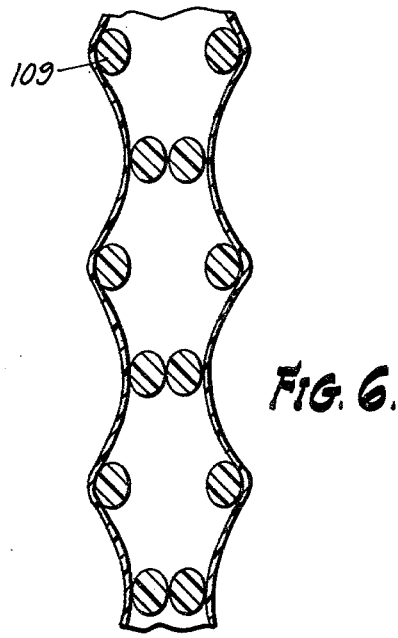

Referring now to FIGS. 4-6, a membrane support structure generally referred to as 103 is shown. The membrane is permanently deformed into the interstices 107 of the fibers 109 of the support structure 103 whereby forming a plurality sinuous passageway 105 between the alternate wrappings of the tubular membrane 83. Such a configuration increases the membrane transfer area and creates turbulence in the fluids on either side of the membrane 83 which aids in the transfer.

Referring again now to FIG. 2, it is understood that any suitable membrane support structure 103, such as an embossed sheet, having a plurality of interstices 107 may be utilized in accordance with this invention. The area between the driven piston 97 and diaphragm 99 and the flaccid membrane 101 is vented so that the action of the piston cannot pull a vacuum on the blood. In other words, the ventricle 93 is a passive, filling device. This is important because under these circumstances, this oxygenator 1 cannot pump air and will only pump that amount of fluid that actually fills the ventricle 93 during the filling cycle. As the piston 97 is withdrawn, fluid from the venous supply is forced through the atrium 57 and around the heat exchanger 51 and through the leaf valve 91 into the ventricle 93. On the upward stroke of the piston 97, whatever fluid is in the ventricle 93 is discharged in a pulsatile fashion through the membrane passages 105 and into the arterial line 33 running to the patient. At each upward of pressure stroke of the piston 97, the annular leaf valve 91 is closed so that blood cannot flow to the atrium 57 and venous system from the ventricle 93. The purpose of the atrium 57 is to absorb the kinetic energy of the flowing venous blood at the time the leaf valve 91 is closed so that there is a more or less continuous flow of venous blood from the patient and this flow is not stopped each time the valve 91 closes. Since the charging gas in the atrium 57 is separated from the blood by slack impermeable membrane 59 there is no blood-gas interface in this portion of the device.

The system functions as follows:

Venous blood from the patient's superior and inferior vena cava flows through the venous line 3 and through the heat exchanger 51 into the atrium chamber 57, and through the annular leaf valve 91 into the ventricle 93. Venous blood continues to flow into the ventricle 93 in this fashion until the up or power stroke is initiated by the power source 95. If the ventricle 93 has not completely filled by the venous flow before the initiation of the up or power stroke, then some of the differences may be made up from blood or fluid flowing from the cardiotomy reservoir 5. When the upward or power stroke is initiated, the annular leaf valve 91 closes which stops all flow into the ventricle 93 from the venous side. However, the venous blood and the fluid, if any, from the cardiotomy reservoir 5 have kinetic energy and continue to flow into the venous atrium 57 so that flow from the patient's vena cava is relatively constant. With the initiation of the upward or power stroke, a pressure pulse is created within the ventricle 93 which passes through the passageways 105 between the membrane 83. This pressure pulse is greater than arterial pressure of the patient and, therefore, a volume of arterial blood is discharged through the arterial line 33, into the patient's arterial system. As the piston 97 retracts, the annular leaf valve 91 reopens due to the venous pressure plus the pressure created by the kinetic energy of the blood in the venous artrium 57 and blood from the venous sytstem flows into the ventricle 93 again. During the first portion of this downward stroke, the arterial blood continues to flow into the artery due to its kinetic energy. However, the arterial kinetic energy is soon dissipated and a small back pulse ensues, helping to fill the ventricle 93 by backflow through the membrane 83. When the next power stroke is initiated, the annular leaf valve 91 again closes and a new pressure pulse is initiated in the arterial system. These pressure pulses, both forward and reverse, create turbulent flow through the pillow-like pattern of the membrane 83 which insures mixing of the hemoglobin and plasma and disturbs the static layer of cells on the membrane increasing the efficiency of transfer.

As soon as the pulse rate has been established, the pressure of the oxygen should be increased so that it is just less than the maximum pulse pressure created by the pulse pumping means 95. Because of the action of the control valve 31, the oxygen pressure will be a maximum at the time the blood pressure is a maximum, and a minimum at the time the blood pressure is a minimum, since the oxygen valve 31 closes to shut off the oxygen exhaust at the initiation of the upward or pressure stroke of the piston 97 and opens to exhaust the oxygen in the system just before the maximum blood pressure is reached. This arrangement of the oxygen system accomplishes two things. First, it maintains the pressure differential across the membrane 83 relatively constant even though the blood pressure is pulsatile and constantly varying. Secondly, it allows a rapid exhaust of the gas trapped between the membrane which tends to clear the water vapor and carbon dioxide from the membrane 83.

The preceding descriptions of specific embodiments should not be construed to limit the scope of the present invention as other modifications within the teaching of this invention may occur to those skilled in the art.

What is claimed is:

1. A membrane fluid transfer device comprising:
    a housing having a process fluid inlet and outlet;
    an atrium chamber means for providing a reservoir for incoming fluid formed within said housing and in communication with said housing process fluid inlet;
    a ventricle connected to said atrium by valving means which substantially restricts blood back flow;
    a spirally wound, flattened, tubular permeable membrane having a transfer fluid inlet at one end of said tubular membrane and a transfer fluid outlet at the opposite end of said membrane, said membrane forming passageways between adjacent windings of said membrane, one end of said passageways being in communication with said ventricle and the opposite end of said passageways being in communication with said housing process fluid outlet;
    said ventricle being further defined as including means for pumping fluid through said passageways between said adjacent windings of said membrane, said ventricle means being connected to said atrium by a fluid passageway having said ventricle valving means positioned within said fluid passageway, said ventricle being in connection with said membrane windings and a portion of said ventricle being formed by a member adapted to be actuated by a driving means; and
    control means for closing said transfer fluid outlet at the initiation of the pressure stroke of said ventricle driving means, and for rapid opening of said transfer fluid outlet and rapid exhalating of transfer fluid from said membrane at the completion of said pressure stroke of said ventricle driving means.

2. The fluid transfer device claimed in claim 1 wherein said tubular membrane is further defined as having a multi-interstice support structure positioned within said tubular membrane.

3. The membrane oxygenator claimed in claim 2 wherein said tubular membrane is permanently deformed into said support structure interstices.

4. A membrane oxygenator comprising:
    a housing having a blood inlet and outlet;
    an atrium chamber means for providing a reservoir for incoming blood formed within said housing and in communication with said housing blood inlet;
    a flaccid, impermeable membrane enclosure occupying a portion of said atrium;
    a ventricle connected to said atrium by valving means which substantially restricts blood back flow;
    a spirally wound, flattened, tubular permeable membrane having an oxygen inlet at one end of said tubular membrane and a valved oxygen and carbon dioxide outlet at the opposite end of said membrane, said membrane forming passageways between adjacent windings of said membrane, one end of said passageways being in communication with said ventricle and the opposite end of said passageway being in communication with said housing blood outlet;
    said ventricle being further defined as including means for pumping fluid through said passageways between said adjacent windings of said membrane, said ventricle means being connected to said atrium by a blood passageway having said valving means positioned within said blood passageway said ventricle being in connection with said membrane windings, and a portion of said ventricle being formed by a member adapted to be actuated by a driving means; and
    control means for closing said oxygen and carbon dioxide outlet valving at the initiation of the pressure stroke of said ventricle driving means, and for rapid opening said oxygen and carbon dioxide outlet valving and rapid exhalating of said oxygen and carbon dioxide from said membrane at the completion of said pressure stroke of said ventricle driving means.

5. The membrane oxygenator claimed in claim 4 wherein said atrium membrane enclosure is filled with a gas at atmospheric pressure.

6. The membrane oxygenator claimed in claim 5 wherein said gas is substantially carbon dioxide, and said carbon dioxide is maintained at a pressure above atmospheric pressure.

7. The membrane oxygenator claimed in claim 4 wherein said ventricle valving means is defined as comprising an annular leaf valve.

8. The membrane oxygenator claimed in claim 4 wherein the area between said ventricle membrane and said driving means is vented.

9. The membrane oxygenator claimed in claim 8 wherein said driving means is further defined as reciprocating between said pressure stroke and a suction stroke.

10. The membrane oxygenator claimed in claim 4 wherein said tubular membrane is formed from an asymetric, thermoplastic material.

11. The membrane oxygenator claimed in claim 10 wherein said tubular membrane material is selected from the group consisting of polysulphane, polycarbonate and copolymers thereof.

12. A membrane oxygenator comprising:
   a housing having an annular heat exchanger positioned therein, said heat exchanger having a heat transfer medium inlet and outlet and a blood inlet and outlet;
   an atrium chamber for providing a reservoir for incoming blood formed by the inner surface of said heat exchanger, a flaccid, impermeable membrane enclosure occupying a portion of said atrium, and said atrium being in communication with said heat exchanger blood outlet;
   a ventricle connected to said atrium by valving means which substantially restricts blood back flow;
   an arterial blood outlet;
   a spirally wound, flattened, tubular permeable membrane having an oxygen inlet at one end of said tubular membrane and a valved oxygen and carbon dioxide outlet at the opposite end of said membrane, said membrane being positioned between the inner surface of said housing and the outer surface of said heat exchanger and forming passageways between adjacent windings of said membrane, one end of said passageways being in communication with said ventricle and the opposite end of said passageways being in communication with said arterial blood outlet;
   said ventricle being further defined as including means for pumping fluid through said passageways between said adjacent windings of said membrane, said ventricle means being connected to said atrium by a blood passageway having said ventricle valving means positioned within said blood passageway said ventricle being in connection with said membrane windings, and a portion of said ventricle being formed by a member adapted to be actuated by a driving means and;
   control means for closing said oxygen and carbon dioxide outlet valving at the initiation of the pressure stroke of said ventricle driving means, and for rapid opening said oxygen and carbon dioxide outlet valving and rapid exhalating of said oxygen and carbon dioxide from said membrane at the completion of said pressure stroke of said ventricle driving means.

13. The membrane oxygenator claimed in claim 12 wherein said heat exchanger is further defined as being a double walled, double helix heat exchanger.

14. The membrane oxygenator claimed in claim 13 wherein said atrium membrane enclosure is charged with carbon dioxide to a pressure above atmospheric pressure.

15. A membrane oxygenator comprising:
   a housing having an annular double walled heat exchanger positioned therein, said heat exchanger having a heat transfer medium inlet and outlet and a blood inlet and outlet;
   an atrium chamber means for providing a reservoir for incoming blood formed by the inner surfaces of said heat exchanger and a flaccid, impermeable membrane enclosure occupying a portion of the atrium volume, said atrium being further defined as being in communication with said heat exchanger blood outlet;
   a ventricle connected to said atrium by valving means which substantially restricts blood back flow;
   a spirally wound, flattened tubular permeable membrane positioned within the inner surface of said housing and the outer surface of said heat exchanger, said tubular membrane having a multiinterstice support structure positioned within said tubular membrane and said membrane being deformed into said support structure interstice, said wound tubular membrane forming passages between adjacent windings of said membrane, one end of said passageways being in communication with said ventricle and the opposite end of said passageways being in communication with said arterial blood outlet, said tubular membrane being further defined as having an oxygen inlet at one end of said tubular membrane and a valved oxygen and carbon dioxide outlet at the opposite end of said membrane;
   said ventricle being further defined as including means for pumping fluid through said passageways between said adjacent windings of said membrane, said ventricle means being connected to said atrium by a blood passageway having said ventricle valving means positioned within said blood passageway said ventricle being in connection with said membrane windings, and a portion of said ventricle being formed by a member adapted to be actuated by a driving means;
   and control means for closing said oxygen and carbon dioxide outlet valving at the initiation of the pressure stroke of said ventricle driving means, and for rapid opening said oxygen and carbon dioxide outlet valving and rapid exhalating of said oxygen and carbon dioxide from said membrane at the completion of said pressure stroke of said ventricle driving means.

16. The membrane oxygenator claimed in claim 15 wherein the area between said ventricle membrane and said driving means is vented to the atmosphere.

17. A membrane oxygenator comprising:
   a housing having an annular double wall heat exchanger positioned therein, said heat exchanger having a heat transfer medium inlet and outlet and a blood inlet and outlet;
   an atrium chamber means for providing a reservoir for incoming blood formed by the inner surfaces of said heat exchanger and a flaccid, impermeable membrane enclosure occupying a portion of the atrium volume, said atrium being further defined as being in communication with said heat exchanger blood outlet;
   a ventricle connected to said atrium by valving means which substantially restricts blood back flow;
   a spirally wound, flattened, tubular, permeable membrane having an oxygen inlet at one end of said tubular membrane and a valved oxygen and carbon dioxide outlet at the opposite end of said membrane, said membrane being formed from a thermoplastic material selected from the group consisting of polysulfone, polycarbonate and copolymers thereof, said tubular membrane being further defined as having a multiinterstice support structure positioned within said tubular membrane and said tubular membrane being permanently deformed into said support structure interstices, said supported tubular membrane being positioned between the inner surface of said housing and the outer surface of said heat exchanger and forming passageways between adjacent windings of said membrane, one end of said passageways being in communication with said ventricle and the opposite end of said passageways being in communication with said arterial blood outlet;

said ventricle being further defined as including means for pumping fluid through said passageways between said adjacent windings of said membrane, said ventricle means being connected to said atrium by a blood passageway having said ventricle valving means positioned within said blood passageway said ventricle being in connection with said membrane windings, and a portion of said ventricle being formed by a member adapted to be actuated by a driving means, the volume between said ventricle and said driving means being vented to the atmosphere; and control means for closing said oxygen and carbon dioxide outlet valving at the initiation of the pressure stroke of said ventricle driving means, for rapid opening said oxygen and carbon dioxide outlet valving and rapid exhalating of said oxygen and carbon dioxide at the completion of said pressure stroke of said ventricle driving means.

18. A membrane oxygenator comprising:
a housing having a blood inlet and outlet;
an atrium chamber means for providing a reservoir for incoming blood formed within said housing and in communication with said housing blood inlet;
a ventricle connected to said atrium by valving means which substantially restricts blood back flow;
a spirally wound, flattened, tubular permeable membrane having an oxygen inlet at one end of said tubular membrane and a valved oxygen and carbon dioxide outlet at the opposite end of said membrane, said membrane forming passageways between adjacent windings of said membrane, one end of said passageways being in communication with said ventricle and the opposite end of said passageways being in communication with said housing blood outlet;

said ventricle being further defined as including means for pumping fluid through said passageways between said adjacent windings and said membrane, said ventricle means being connected to said atrium by a blood passageway having said ventricle valving means positioned within said blood passageway said ventricle being in connection with said membrane windings, and a portion of said ventricle being formed by a member adapted to be actuated by a driving means;

control means for closing said oxygen and carbon dioxide outlet valving at the initiation of the pressure stroke of said ventricle driving means, for rapid opening said oxygen and carbon dioxide outlet valving and rapid exhalating of said oxygen and carbon dioxide at the completion of said pressure stroke of said ventricle driving means.

19. A method for varying the properties of blood across a membrane comprising:
drawing said blood to be processed into a ventricle chamber;
pumping said blood to be processed through passageways formed between adjacent exterior surfaces of a wrapped, oxygenating membrane;
forcing a transfer fluid into the interior of said wrapped oxygenating membrane;
controlling the rapid exhalating of the transfer fluid and any substances removed from the blood through said membrane and said pumping of blood to be processed, whereby beginning said exhalating at the completing of the pumping and completing said exhalating at the beginning of said pumping.

20. The method of processing blood across a membrane claimed in claim 19 wherein said method is further defined as producing turbulence of said pumping of said blood to be oxygenated by passing said blood over and through membrane covered multi-interstice passageways with a continuously varying velocity and pressure pulse profile.

21. A method for oxygenating blood across a membrane comprising:
drawing said blood to be oxygenated into a ventricle chamber;
pumping said blood to be oxygenated through passageways formed between adjacent exterior surfaces of a wrapped, oxygenating membrane;
forcing oxygen into the interior of said wrapped oxygenating membrane; and
controlling the rapid exhalating of oxygen and carbon dioxide from said oxygenating membrane and said pumping of blood to be oxygenated, whereby beginning said rapid exhalating at the completing of the pumping and completing said exhalating at the beginning of said pumping and maintaining a substantially constant differential pressure across said membrane during said pumping.

22. The method of oxygenating blood across a membrane claimed in claim 21 wherein said method further comprises transferring oxygen through said membrane into said blood, and transferring carbon dioxide from said blood across said membrane into the main oxygen stream.

23. The method of oxygenating blood across a membrane claimed in claim 21 wherein said method is further defined as producing turbulence of said pumping of said blood to be oxygenated by passing said blood over and through membrane covered multi-interstice passageways with a continuously varying velocity and pressure pulse profile.

24. A method for oxygenating blood across a membrane comprising:
exchanging heat between said blood to be oxygenated and a heat transfer medium thereby controlling said blood temperature;
storing said blood to be oxygenated in an atrium;
containing a flaccid impermeable membrane thereby compressing said atrium membrane;
drawing said blood to be oxygenated into a ventricle chamber;
pumping said blood to be oxygenated through passageways formed between adjacent exterior surfaces of a wrapped, oxygenating membrane;
forcing oxygen into the interior of said wrapped oxygenating membrane;
controlling the rapid exhalating of oxygen and carbon dioxide from said oxygenating membrane and said pumping of blood to be oxygenated, whereby beginning said rapid exhalating at the completing of the pumping and completing said exhalating at the beginning of said pumping and maintaining a substantially constant differential pressure across said membrane during said pumping.

* * * * *